US 6,551,243 B2

(12) United States Patent
Bocionek et al.

(10) Patent No.: US 6,551,243 B2
(45) Date of Patent: Apr. 22, 2003

(54) SYSTEM AND USER INTERFACE FOR USE IN PROVIDING MEDICAL INFORMATION AND HEALTH CARE DELIVERY SUPPORT

(75) Inventors: Siegfried Bocionek, Nuernberg (DE); Margo Hanslik, Erlangen (DE); Siegfried Russwurm, Michelau (DE)

(73) Assignee: Siemens Medical Solutions Health Services Corporation, Malvern, PA (US)

( * ) Notice: Subject to any disclaimer, the term of this patent is extended or adjusted under 35 U.S.C. 154(b) by 0 days.

(21) Appl. No.: 09/899,798

(22) Filed: Jul. 5, 2001

(65) Prior Publication Data

US 2002/0099273 A1 Jul. 25, 2002

Related U.S. Application Data

(60) Provisional application No. 60/263,790, filed on Jan. 24, 2001.

(51) Int. Cl.[7] ................................................ A61B 5/00
(52) U.S. Cl. ...................................... 600/300; 128/923
(58) Field of Search ............................... 600/300, 301; 705/2, 3; 128/903, 904, 920–925

(56) References Cited

U.S. PATENT DOCUMENTS

| 5,713,350 | A | | 2/1998 | Yokota et al. | |
|---|---|---|---|---|---|
| 5,724,580 | A | * | 3/1998 | Levin et al. | 705/2 |
| 5,738,102 | A | * | 4/1998 | Lemelson | 128/903 |
| 5,772,585 | A | | 6/1998 | Lavin et al. | 600/300 |

(List continued on next page.)

FOREIGN PATENT DOCUMENTS

| DE | 19922 793 A1 | 7/2000 |
|---|---|---|
| WO | WO 98/29790 | 7/1998 |

OTHER PUBLICATIONS

Inchingolo: "L'Integrazione PACS, RIS E HIS" Relazione Congresso NAZ. ANMDO, Nov. 21, 1998, pp. 16–22 XP–002206925.

F. J. Martens et atl.: HIPIN, a working HIS/RIS–PACS interface EUROPACS Newsletter, Online! vol. 10, No. 1, Feb. 1997, pp. 1–3 XP002206926 http://www.rad.unipi.it.

Hewlett Packard HP M2000A Central Data Management for the Critical Care Environment Technical Information Revision C.02.

(List continued on next page.)

*Primary Examiner*—Eric F. Winakur
*Assistant Examiner*—David J. McCrosky
(74) *Attorney, Agent, or Firm*—Alexander J. Burke

(57) ABSTRACT

A medical information system processes information from multiple sources suitable for access by healthcare personnel for use in clinical (e.g., critical) care delivery. The system includes a communication interface for receiving information from patient monitoring devices and for bidirectionally communicating with a hospital information database containing patient records. The system also includes a data processor using the communication interface for acquiring patient record information from the hospital information database and for acquiring information from patient monitoring devices. The data processor updates the acquired patient record information based on the acquired information from the patient monitoring devices and communicates updated patient record information to the hospital information database, A display processor initiates display of the updated patient record information to a user. The data processor may also include a data analysis unit for analyzing stored patient parameters by correlating stored parameters, patient record information, corresponding medical outcomes and medication database information to identify alternative medication options and improve decision processing. The data processor combines acquired medical parameter information and an acquired patient medical image to provide a composite image for display and storage.

22 Claims, 3 Drawing Sheets

U.S. PATENT DOCUMENTS

| | | | | |
|---|---|---|---|---|
| 5,827,180 A | * | 10/1998 | Goodman | 600/300 |
| 5,911,687 A | | 6/1999 | Sato et al. | 600/300 |
| 5,924,074 A | | 7/1999 | Evans | 705/3 |
| 6,014,631 A | * | 1/2000 | Teagarden et al. | 705/2 |
| 6,024,699 A | * | 2/2000 | Surwit et al. | 600/300 |
| 6,047,259 A | | 4/2000 | Campbell et al. | 705/3 |
| 6,139,494 A | * | 10/2000 | Cairnes | 600/300 |
| 6,208,974 B1 | | 3/2001 | Campbell et al. | 705/3 |
| 6,234,964 B1 | * | 5/2001 | Iliff | 600/300 |
| 6,371,123 B1 | * | 4/2002 | Stark et al. | 600/300 |

OTHER PUBLICATIONS

Solar Unit Manager System General Information.

Meta vision Tour—Workflow Support.

Agilent Technologies; Agilent/Healthcare—Patient Monitoring.

Physician Review System Functionality Comparison.

Tour Analysis When time is of the essence.

Tour data entry When time is of the essence.

Patient Administration Demo Center.

HP Viridia Patient Documentation Center M2000A Technical Data Sheet.

Inchingolo: "L'Integrazione PACS, RIS E HIS" Relazione Congresso NAZ. ANMDO, Nov. 21, 1998, pp. 16–22 XP–002206925 with translation.

* cited by examiner

SYSTEM AND USER INTERFACE FOR USE IN PROVIDING MEDICAL INFORMATION AND HEALTH CARE DELIVERY SUPPORT

This is a non-provisional application of provisional application serial No. 60/263,790 by S. Bocionek et al. filed Jan. 24, 2001.

FIELD OF THE INVENTION

This invention concerns a comprehensive information system and architecture for use in clinical care delivery and optimization.

BACKGROUND OF THE INVENTION

Critical care delivered in ICUs (Intensive Care Unit), ERs (Emergency Room), ORs (Operating Rooms), for example, and some other specialized clinical settings, is an area of medicine where improvements have significant life or death impact. As a minimum such improvements ameliorate the critical condition of patients treated there. Specialized personnel (doctors, nurses), equipment (monitors, infusion devices, ventilators, vital sign detectors, etc.), highly efficient drugs and special-purpose disposable devices (e.g. catheters) contribute to the success of critical care delivery. An important component in this setting is the information processed. Specifically, information elements of importance include the available data on the patients history and daily improvement, vital signs indicating patient status and stability, medication plans, but also medical knowledge in general and broad personnel experience (i.e. knowledge gained from a large number of cases) by doctors and nurses.

Each of the above critical care contributors are periodically examined and hopefully improved. However, such improvement tends to occur in a haphazard and piecemeal manner. For example, new ventilators with sophisticated gas valve controls refine the dosage of anesthesia applied with gas to improve patient care. Also smart alarms generate alarm indications from combined vital signs thereby helping to avoid unnecessary calls of the nurses, and better focus attention on critical situations that are real.

Despite such limited optimization of the components in critical care and other clinical settings, further improvement is possible by combining smart devices, integrated information processing, and aggregated knowledge derived form large case databanks.

A system according to invention principles delivers such improvement and addresses associated problems.

SUMMARY OF INVENTION

A system holistically improves critical care delivery by providing a technical combination of medical information processing devices providing flexible parallel access to static and dynamic patient data as well as medical information relevant for a particular application. A medical information system processes information from multiple sources suitable for access by healthcare personnel for use in clinical (e.g., critical) care delivery. The system includes a communication interface for receiving information from patient monitoring devices and for bidirectionally communicating with a hospital information database containing patient records. The system also includes a data processor using the communication interface for acquiring patient record information from the hospital information database and for acquiring information from patient monitoring devices. The data processor updates the acquired patient record information based on the acquired information from the patient monitoring devices and communicates updated patient record information to the hospital information database. A display processor initiates display of the updated patient record information to a user.

In a feature of the invention, the system includes a data analysis unit for analyzing stored patient parameters by correlating stored parameters, patient record information, corresponding medical outcomes and medication database information to identify alternative medication options and improve decision processing.

In another feature of the invention, the data processor combines acquired medical parameter information and an acquired patient medical image to provide a composite image for display and storage.

DETAILED DESCRIPTION OF PREFERRED EMBODIMENTS

Figure 1:
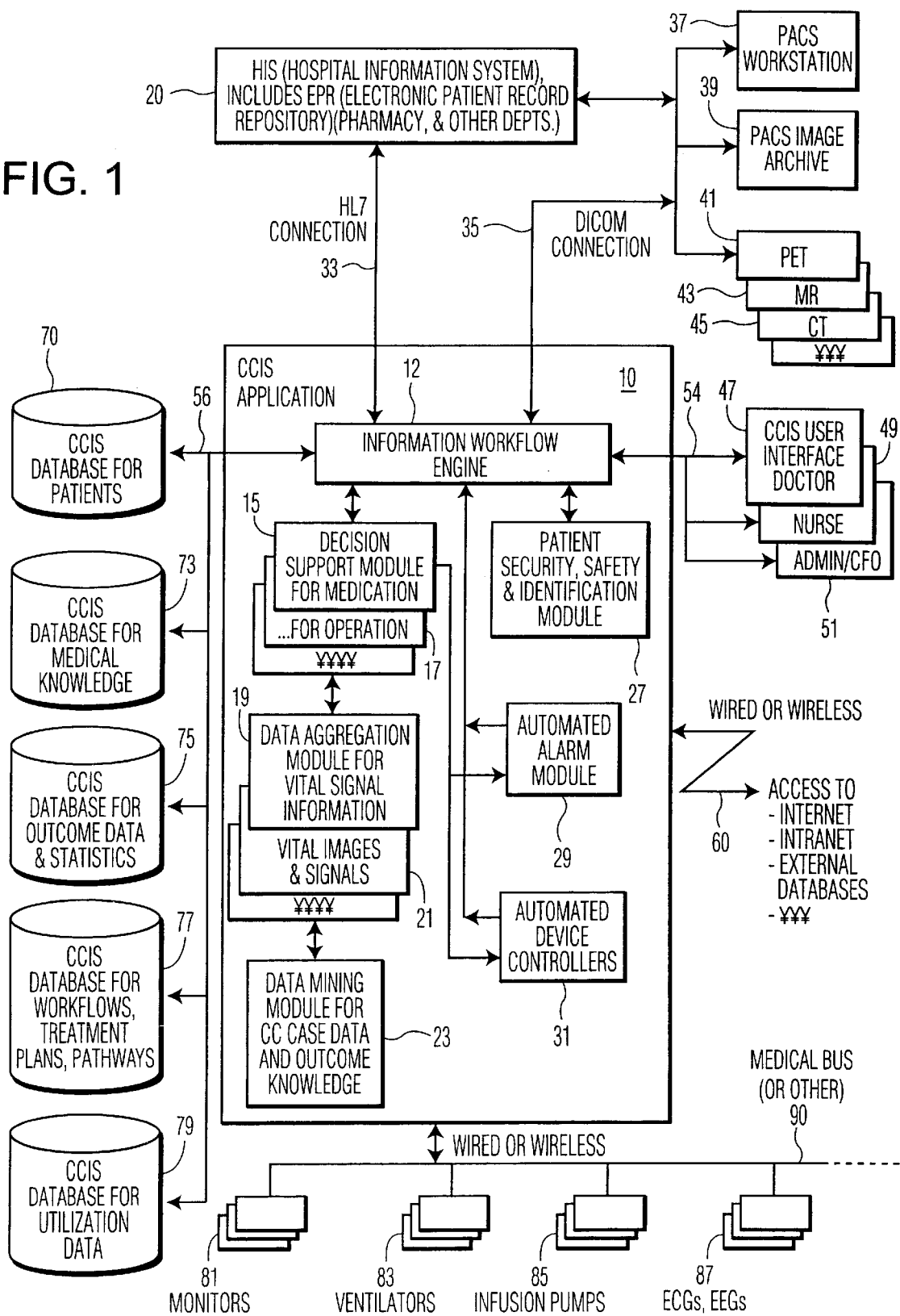
FIG. 1 shows a system for providing medical information and health care delivery support, according to invention principles.

FIG. 1 shows a system for providing medical information and health care delivery support. The system advantageously provides a combination of medical and IT devices, and flexible parallel access to static and dynamic patient data, as well as medical information relevant for a particular case. The system advantageously improves clinical care delivery in critical care or other setting in a holistic manner. Currently available systems provide limited capability and fail to provide the comprehensive features of the disclosed system. Currently available systems supply limited combinations of information or devices, e.g. for aggregation of vital signs (ECG, blood pressure, $O_2$ content) by means of fuzzy logic. Other CCIS systems (critical care information systems) maintain patient data (static, and some vital signals), but exclude other accessible information. These systems also integrate critical care devices using particular dedicated medical bus connections and protocols. Further, although known systems provide access to medical knowledge databases (medical "book knowledge" as well as large case/outcome databases), through the Internet or via database browsers, this access is not integrated into the critical care information flow.

A medical information system according to invention principles processes data of wider variety from a broader range of sources than hitherto achieved. The system processes substantially all available data and information relevant to a critical care need. The location of the information is largely immaterial since the system architecture accesses data from a comprehensive array of networks and devices (including local and remote databases and Internet locations etc.). The medical information system advantageously acquires patient record information from a hospital information database, medical parameter information from patient monitoring devices and patient images from an archive. The system updates the acquired patient record information in view of acquired information from the patient monitoring devices as well as to record generated prescription or treatment information. Updated patient record information is communicated to the hospital information database. System data analysis and decision units advantageously analyze stored patient parameters by correlating stored parameters, patient record information, corresponding medical outcomes and medication database information to suggest treatments and prescriptions and to identify alternative medication options and adaptively improve decision processing. The system also advantageously combines acquired medical parameter information and an acquired patient medical image to provide a composite image for display and storage in an archive. The disclosed system is particularly useful in complex critical care environments including stroke units, interventional angiography rooms, neuro surgery ORs, and transplantation centers, etc. . In these environments, the disclosed system yields improved care, reduced patient risk and improved clinical care delivery quality and efficiency by the provision of access to a wide variety of information sources combined with fast information processing guided by intelligent decision making.

The medical information system of FIG. 1 comprises a critical care information system (CCIS) application 10 communicating with devices via local area networks (LANs) or wide area networks (WANs) as well as communicating via the Internet and other telecommunication (including wireless or landline) networks. The CCIS is Internet Protocol (IP) compatible but may also employ other protocols such as, for example, X.25, frame relay, IBM SNA etc. and may use any type of network architecture that provides communication connectivity among the networked devices. CCIS application 10 resides in a CCIS server however, in other embodiments CCIS application 10 may reside at any remote or local level of network hierarchy since the different levels of the network are interconnected. Alternatively, CCIS application 10 may be executed as a local application within a PC or within a dedicated CCIS device, for example.

CCIS application 10 of FIG. 1 includes information workflow engine 12 for determining medical process task sequences, decision support modules 15 and 17 for medication and operations related decision making respectively and data aggregation processors 19 and 21 for aggregating medical parameters (including vital signs) and images. CCIS application 10 also includes a data mining module 23, a patient security and identification module 27, an alarm module 29 and device controllers 31. CCIS application 10 bidirectionally communicates with Hospital Information System (HIS) 20 patient record repository and other hospital departments typically via an HL7 (Health Level Seven) protocol interface 33 (other interface protocol connections are also possible). Thereby CCIS application 10 accesses and updates patient records retained in the hospital EPR (Electronic Patient Record) repository. CCIS application 10 also accesses data from other HIS 20 departmental systems including a patient management and accounting system, a Radiology Information System (RIS), a Laboratory Information System (LIS), and a hospital Pharmacy. CCIS application 10 accesses and processes the information available from HIS 20 using decision modules 15 and 17, data aggregation modules 19 and 21 and data mining module 23. The processed information is collated and stored in local databases 70–79. Thereby, patient record data and history from the HIS 20 repositories is accessed, processed and displayed on monitor 81 via interface 90. In addition, patient record updates are advantageously communicated to HIS 20 repositories in a synchronous fashion.

The modules and functions of CCIS application 10 are advantageously able to access and update patient record information in HIS 20 using a Master Patient Index (MPI) stored within HIS 20. The access process is governed by security and identification unit 27 which ensures that a patient is correctly identified by resolving patient record anomalies including patient name errors, name duplications and patient record and name mismatches. For this purpose unit 27 supports multiple Patient Identification Scheme (PIDS) standards including those of HL7 and CORBAmed (a derivative standard of the Common Object Request Broker Architecture by a task force of the Object Management Group). Unit 27 typically identifies a patient based on patient name, birthdate and sex as primary identifiers and may also employ social security number and patient address. Unit 27 creates a unique number based on these parameters and uses this unique number for internal patient identification. In accessing other systems, unit 27 maps the unique number to corresponding patient identifiers used by these other systems. Unit 27 employs known security protocols including the SSL (secure socket layer) protocol and RSA public key encryption in managing access to patient records and the Master Patient Index. Other security protocols may also be used for this purpose CCIS application 10 accesses medical image data from PACS (Picture Archiving and Communication System) compatible archive 39 and workstation 37 or directly from diagnostic units such as PET (Positron Emission Tomography) unit 41, MR (Magnetic Resonance) unit 43 or CT (Computed Tomography) unit 45. Image data is accessed by CCIS application 10 via interface 35 using DICOM (Digital Imaging and Communications in Medicine) standard (published approx. 1990). CCIS application 10 also accesses medical parameters from patient monitoring devices including ventilators 83, infusion pumps 85, electrocardiograph (ECG) and electroencepholograph (EEG) units 87, blood oxygen detectors, pulse detectors and anesthesia units (not shown) and other devices via bus interface 90. Interface 90 is typically a known medical industry standard Medical Interface Bus (MIB) used for locally interconnecting medical devices in a patient's room, for example, for both display and control to administer care and monitor a particular patient. Alternatively, bus 90 may be a different type of wired or wireless bus, such as an Ethernet-compatible LAN.

CCIS application 10 advantageously accesses both patient image data and patient medical parameters and combines the medical parameters and image data to form a composite image for display and storage in archive 39. Therefore, CCIS application 10 is able to combine a vital sign from the critical care setting, such as an ECG or EGG signal from unit 87, with a patient brain image (e.g., identifying a dead area detected by a PET unit after a stroke) or a patient heart image (e.g., identifying damage after a myocardial infarct) to form a composite image. The aggregation of such a vital sign and functional image is performed by data aggregation units 19 and 21 in conjunction with decision units 15 and 17.

Consequently, a patient image from a PACS compatible archive or from a diagnostic unit such as a PET, MR, Ultrasound, or other unit may be advantageously displayed, evaluated and manipulated on a critical care patient monitor 81 directly in a patient critical care bedside location.

CCIS application 10 incorporates Information workflow engine 12 for the definition and generation of detailed task sequences and associated control operations supporting tasks or processes used in clinical care delivery. Workflow engine 12 does this in response to task commands, requests and inputs received from either HIS 20, from healthcare personnel via direct user interfaces 47–51, from monitors and patient monitoring devices 81–87, or from external users via interface 60. Specifically, in response to task commands, workflow engine 12 generates and maintains detailed task lists (worklists) and controls decision processors 15 and 17, data aggregation processors 19 and 21 and data search and mining processor 23 in generating and implementing workflow task sequences. In responding to task commands, CCIS application 10 in conjunction with workflow engine 12 may generate individual, intermittent or periodic messages for communication to other units. This may include deriving and combining vital sign parameters using units 19 and 21 and communicating the derived signals to automated alarm unit 29, for example. Further, workflow task sequences generated by workflow engine 12 are stored in database 77 and are advantageously dynamically updated to incorporate improvements identified by analyzing treatment and associated medical outcome results for either an individual patient or for multiple patients. The data analysis involves searching patient records in multiple patient medication and treatment databases for statistically significant data correlations and patterns identifying treatment features leading to verifiable improvement. Such multiple patient medication and treatment databases may comprise local databases (e.g., database 75) or a remote database accessible via interface 60 involving an Internet or other network protocol.

CCIS application 10 also advantageously acquires, tracks and stores a variety of resource utilization data for both goods and services in database 79 for inspection by healthcare personnel including doctors, nurses and administrators via respective interfaces 47, 49 and 51. Interfaces 47–51 together with CCIS application 10 permit a user to search, query, collate and display desired resource utilization data in a user selectable format. The resource utilization data monitors time and services provided by personnel including doctors and nurses for specific treatment purposes. Similarly, the resource utilization data also monitors use of goods including drugs, disposable medical goods, infusion liquids, equipment accessories and other items. CCIS application 10 further analyzes the stored data to identify typical or normal cost guideline thresholds and treatment cases exceeding normal cost thresholds. CCIS application 10 thereby identifies cost reduction and containment opportunities and assists in investment and planning and other financial control activities.

Decision support modules 15 and 17 of CCIS application 10 are used for supporting, diagnosis and associated medication and prescription selection using local or remote databases of medical information and known standard medical data access codes. In particular, decision functions 15 and 17 generate prompts, medication selection guidance and warnings through alert and guidance display elements displayed via user interfaces 47 and 49. A generated warning may indicate a patient drug-allergy or a potential drug to drug interaction that may lead to an "adverse event" for the patient, for example. Further, decision functions 15 and 17 respond to specific medication and medical condition questions submitted by a user via query display elements presented via interfaces 47 and 49. A doctor may submit a query via interface 47 to determine what medication is best in a current situation, for example.

Decision functions 15 and 17 also access patient vital signs and corresponding vital images for improved decision processing. A particular improvement is derived from superimposing color-coded ECG or EEG signals, for example, on an associated anatomical structure image (e.g., a PET image, or functional MR image). This superimposition aids the identification of conditions supporting a diagnosis or medication prescription by indicating the conjunction of a corresponding anomaly occurring in both an image and a vital sign trace. The identification of image anomalies is supported by an image interpretation algorithm employing known techniques including automatic edge detection, semi-automatic area segmentation and analysis and image comparison with standard images obtained from an archive or library, for example. Alternatively, the identification of image anomalies may be performed manually by a doctor. In this case, image anomaly identification data and interpreted characteristic information may be entered by the doctor via interface 47 for use by decision modules 15 and 17.

Decision functions 15 and 17 employ data aggregation functions 19 and 21 as well as data searching and mining function 23 for processing data from various sources. These sources include patient monitoring and associated equipment sources (81, 83, 85 and 87), various databases (70, 73, 75 and 79), general patient information from sources like the HIS 20, image stores (37, 39), image generating devices (41, 43 and 45) and external data and knowledge sources accessed via interface 60 using the Internet or other access mechanisms. Data aggregation functions 19 and 21 identify data patterns, statistical correlations and data anomalies suggestive of potential treatment improvements. Aggregation functions 19 and 21 further test identified improvements against known medical knowledge and available patient record and parameter databases for verification. Resulting conclusions comprise improved decision rules and thresholds, treatment plans, workflow triggers and other medical conclusions. Data aggregation units 19 and 21 also monitor the performance of the aggregation function internal operation including the algorithms used in deriving the conclusions and adaptively improve the aggregation function operation by tailoring the algorithms based on the monitored performance. This feedback mechanism yields dynamic improvement of aggregation functions 19 and 21 and thereby yields dynamic improvement in treatment workflow task sequences and associated control operations.

Data mining function 23 searches the available information sources for relevant data for processing by aggregation functions 19 and 21. The relevant data is processed by aggregation functions 19 and 21 in identifying data correlations and patterns from combinations of parameters indicating statistically significant conclusions, as previously discussed. Data mining function 23 advantageously employs known standard medical condition code sets and associated category or class code sets and medical terminology in searching available information sources. For this purpose data mining function 23 associates corresponding codes and terminology of different code and terminology sets by a map. The map is used in associating and acquiring desired information elements from different information sources employing different information code and category classifications.

Decision support functions 15 and 17, in conjunction with data aggregation functions 19 and 21 and data mining function 23, determine new or improved treatment solutions or processes (including workflow task and control sequences). The improved workflow task sequences, treatment solutions and processes are substituted for the existing workflow task sequences, treatment solutions and processes stored in database 77. Further, derived knowledge and data are stored in databases 73, 75, and 79 and communicated via interface 60 to remote databases. Decision support functions 15 and 17 in conjunction with aggregation functions 19 and 21 and alarm function 29 also provide intelligent automated alarm control in the critical care setting. Alarm function 29 generates an alarm based on individual, composite or weighted composite vital signs from units 81-87 via bus 90 and additional information from decision support functions 15 and 17. Decision support functions 15 and 17 derive conclusions based on available medical data and patient vital signs and parameters and optimize alarm function 29 settings and thresholds.

Further, device controller 31 in conjunction with decision functions 15 and 17 intelligently control devices including ventilator 83 and infusion pump 85. Decision support functions 15 and 17 determine optimal drug dosage to be applied by infusion pump 85 based on the available vital signs and available medical data and knowledge using a closed feedback loop tracking and control mechanism.

Figure 2:
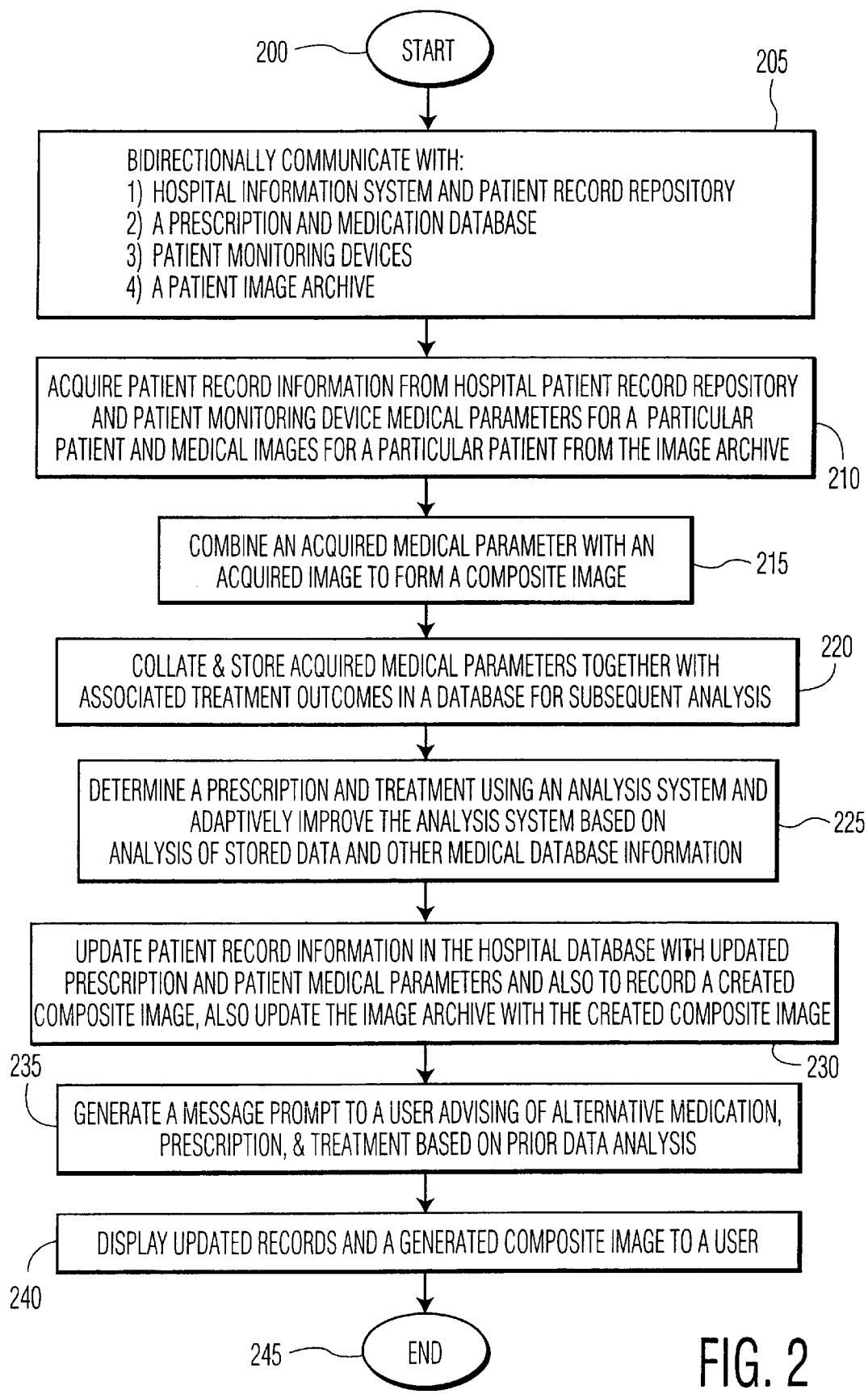
FIG. 2 shows a flowchart of a process for providing and storing medical information including prescription and treatment recommendations for clinical care delivery support, according to invention principles.

FIG. 2 shows a flowchart of a process employed by CCIS application 10 for providing and storing medical information including prescription and treatment recommendations for clinical care delivery support. In step 205 following the start at step 200, CCIS application 10 (FIG. 1) establishes bidirectional communication with HIS 20 via bus 33 and also establishes communication with patient monitoring devices 81–87 via bus 90. CCIS application 10 also establishes communication with image archive 39 via bus 35 and treatment medication and prescription databases 73–79 via bus 56 and external databases via interface 60. In step 210, CCIS application 10 acquires medical parameters for a particular patient from devices 81–87, a patient record for the patient from a record repository in HIS 20 and a medical image for the patient from archive 39. The acquired medical parameters may include some or all of electrocardiograph (ECG) data, electro-encepholograph (EEG) data, ventilation data, blood oxygen data, blood pressure data, infusion pump data and pulse data.

In step 215, CCIS application 10 combines a selected medical parameter and the image data to form a composite image for display and storage in archive 39. The selected medical parameter and image that are combined concern a common anatomical organ, feature or function. For instance, a color PET image of a brain may be combined with an EEG signal to verify information about dead tissue areas. Also a CT vessel image may be combined with a blood pressure signal for use in estimating the risk of a thrombosis or a vessel rupture (since a CT image shows plaque, i.e. narrowed vessel, an increased blood pressure would tend to indicate a narrowed vessel). CCIS application 10, in step 220, collates and stores the acquired medical parameters together with any associated treatment outcome data in local or remote databases for subsequent analysis.

In step 225, CCIS application 10 applies an internal analysis system in determining a prescription and proposed treatment for the patient based on analysis of the stored data including the composite image. CCIS application 10 also adaptively updates and improves the analysis system based on stored data including treatment outcome data. In step 230, CCIS application 10 updates the patient record to reflect the determined prescription and proposed treatment and also to indicate the creation and storage of the composite image and acquired patient monitor information. The updated patient record information is stored in the local patient record repository of database 70 and is subsequently communicated to the HIS 20 patient record repository for synchronized storage. The updated patient record information is communicated to the HIS 20 patient record repository in response to the detection of a patient record alteration in local database 70. Alternatively, the updated patient record information is communicated to the HIS 20 patient record repository in response to other conditions such as, upon user command, upon predetermined intermittent intervals, upon termination of execution of CCIS application 10, or interruption of communication by CCIS 10 with HIS 20, for example.

The patient record contents of local patient record repository 70 and the remote patient record contents of the HIS 20 patient record repository may be matched by known mechanisms such as by a messaging mechanism, for example. Using such a mechanism, one of the databases (e.g. HIS 20 repository) receives an update message from the other database (e.g., database 70) and locates a record for update based on predetermined common data field information, (e.g., a common patient name or identifier). The located record field is updated using received message content. In another embodiment, CCIS application 10 and HIS 20 may share a common database, for example, and either CCIS application 10 or HIS 20 make updates to records stored in the database. Thereby, database 70 replicates the patient record repository in HIS 20.

A message prompt is generated by CCIS application 10 in step 235 for display to a user on monitor 81 or interface displays 47 and 49. The message prompt is generated based on the analysis performed in step 225 and comprises, a warning of a potential problem of a proposed prescription, a suggested alternative prescription, medication or treatment, or advice to a user to check a patient condition affecting a proposed prescription. CCIS application 10 in step 240 initiates display of updated patient record information or a composite image to a user via monitor 81 or displays 47 and 49. The process of FIG. 2 terminates in step 245.

Figure 3:
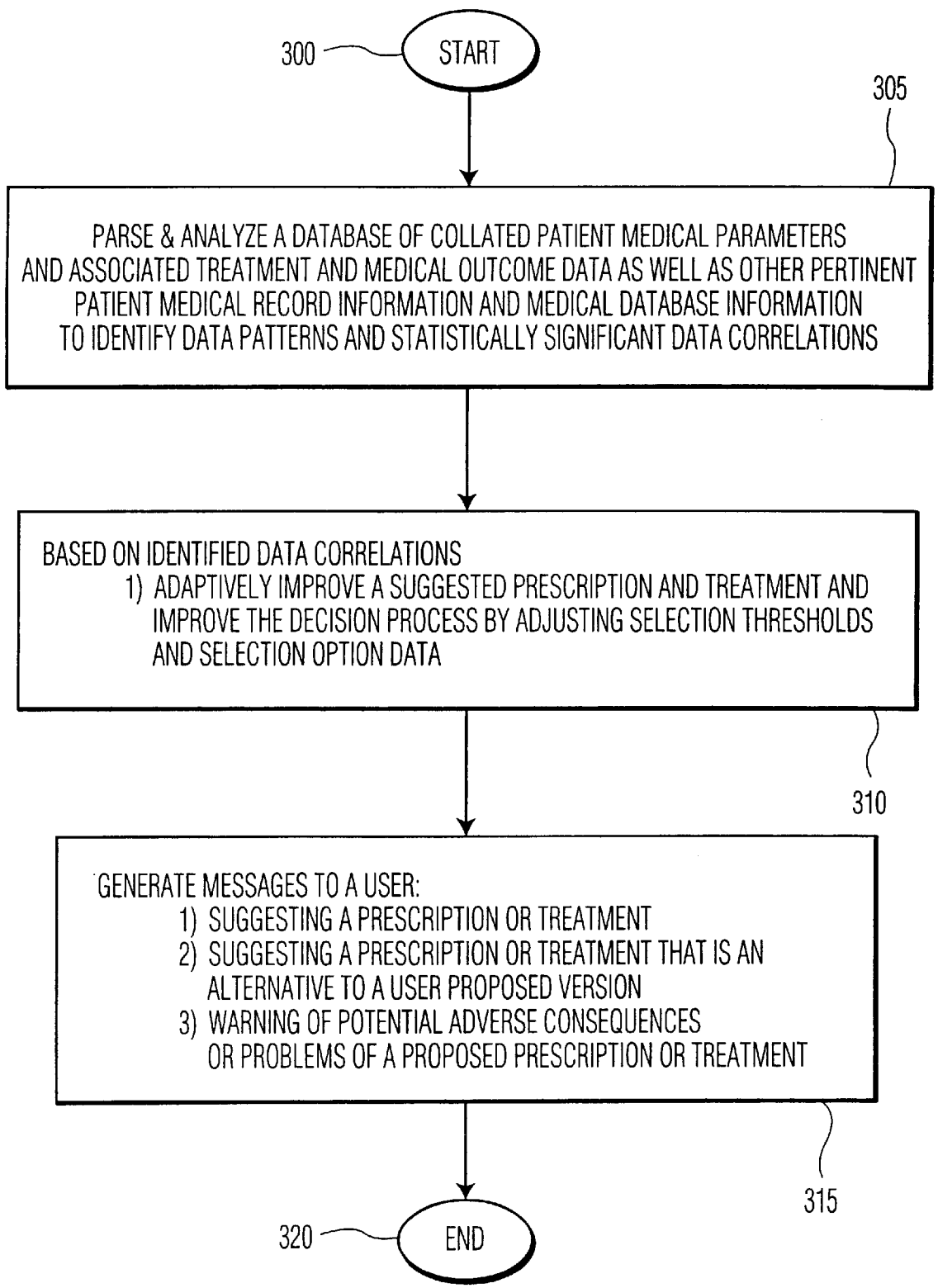
FIG. 3 shows a flowchart of a process for analyzing stored patient parameters, patient record information, medication information and corresponding medical outcomes for deriving treatment improvements and adaptive system improvements, according to invention principles.

FIG. 3 shows a flowchart of a process for analyzing stored patient parameters, patient record information, medication information and corresponding medical outcomes for deriving treatment improvements and adaptive system improvements. In step 305 following the start at step 300, CCIS application 10 parses and analyzes medical information from multiple sources to identify data patterns and statistically significant data correlations in order to identify potential treatment improvements and internal system and algorithm improvements. The multiple medical information sources examined comprise collated patient medical record information, patient medical parameters and associated treatment outcome data as well as pertinent medical information available in local databases 70–79 (FIG. 1) and external databases available via interface 60.

CCIS application 10 in step 310 adaptively improves a prescription and treatment suggestion and decision process by adjusting selection thresholds and selection option data to tailor the prescription process to select the treatments shown to have produced the most favorable outcomes in the analyzed cases. Specifically, this involves refining one or more threshold values that determines the level at which one or more particular medical input parameters (e.g. monitored patient data) suggest the use of one treatment in preference to a different alternative treatment. Similarly, the set of treatment and prescription options available for selection in this manner is reviewed and potentially updated to include those treatments and medications shown to have produced the most favorable outcomes in the analyzed cases and to remove inferior, redundant or harmful treatment and medication options. Either individual or multiple threshold values may be involved and adaptively adjusted in diagnosing treatment for a particular condition. A medical condition may be indicated by the combination of temperature exceeding 39 Celsius and blood pressure or blood oxygen level being below a particular level, for example. Further, threshold values may have a range of values that are associated with corresponding physical conditions such as physical posture, physical activity or other medical conditions and either the range of threshold values or particular threshold values (corresponding to particular conditions) within the range may be adaptively adjusted.

In step 315, CCIS application 10 initiates generation of a message based on the analysis of step 305 for display to a user on monitor 81 or interface displays 47 and 49 (FIG. 1). The message prompt comprises, a suggested prescription or treatment, a suggested alternative prescription or treatment to a user proposed version, or a warning of potential adverse consequences or problems of a proposed treatment or medication.

The architectures and processes presented in FIGS. 1–3 are not exclusive. Other architectures and processes may also be derived in accordance with the principles of the invention to accomplish the same objectives. Further, the inventive principles may be advantageously employed in any clinical health care delivery system for accelerating and accurately guiding decision making based on data accessed from a wide variety of information sources.

What is claimed is:

1. A medical information system for processing information from a plurality of sources suitable for use in critical clinical care delivery, comprising:

a communication interface for receiving medical parameters from patient monitoring devices attached to a particular patient and for bidirectionally communicating with a hospital information database containing patient records;

a data processor using said communication interface for acquiring patient record information for said particular patient from said hospital information database and for collating and storing received medical parameters for said particular patient from monitoring devices; and a decision processor supporting making of a treatment decision concerning a patient medical condition by suggesting at least one treatment based on passively acquired medical parameters received from said monitoring devices independently of patient interaction and processed by said decision processor to support treatment decision making concurrently with patient monitoring and using a treatment information database.

2. A system according to claim 1, wherein said medical parameters are received and processed in substantially real-time, and said passively acquired medical parameters received from said monitoring devices independently of patient interaction comprise medical parameters acquired without said particular patient being required to interactively respond to questions and including an output processor for communicating said suggested treatment for presentation to support physical application of said treatment to said patient by a healthcare worker.

3. A system according to claim 1, wherein said medical parameters are received substantially in real-time and comprise parameters indicative of vital signs sampled at intervals of less than 10 minutes to be suitable to support interventional critical care decision making in at least one of, (a) an Intensive Care Unit (ICU), (b) an Operating Room (OR) and (c) an Emergency Room (ER).

4. A system according to claim 1, wherein said treatment information database includes historical treatment and outcome data for a plurality of patients and said decision processor suggests a treatment based on at least one of, (a) a received patient parameter exceeding a predetermined threshold value and (b) a received patient parameter being outside a value range determined by upper and lower predetermined threshold values and an individual predetermined threshold value is derived from processing historical data comprising a plurality of threshold values associated with treatment provided to a corresponding plurality of different patients and contained in said treatment information database.

5. A system according to claim 4, wherein said medical information system includes a data analyzer for intermittently parsing and analyzing stored collated medical parameters from a plurality of patients in said treatment information database to identify an improved threshold value based on previous treatment outcomes and to adaptively update said threshold value to said improved threshold value.

6. A system according to claim 1, including an update processor for initiating updating of said patient record information to record a determined treatment.

7. A system according to claim 1, wherein said decision processor identifies a complication involved in using a particular treatment for said patient.

8. A medical information system for processing information from a plurality of sources suitable for use in critical clinical care delivery, comprising:

a communication interface for receiving medical parameters from patient monitoring devices and for receiving information from a treatment information database and for bidirectionally communicating with a hospital information database containing patient records;

a data processor using said communication interface for acquiring patient record information for a particular patient from said hospital information database; and a decision processor supporting making of a treatment decision concerning a patient medical condition by suggesting at least one treatment based on, passively acquired medical parameters received from said monitoring devices independently of patient interaction and processed by said decision processor in substantially real-time to support treatment decision making concurrently with patient monitoring and said acquired particular patient record information and information from said treatment information database.

9. A system according to claim 8, including a repository of accumulated utilization data determining usage rates of at least one of, (a) medical goods and (b) medical services in treatment of different medical conditions for a plurality of patients and a data analyzer for analyzing said utilization data to identify a cost threshold representative of an expected cost limit and for using said threshold in identifying a treatment case exceeding said expected cost limit.

10. A system according to claim 8, wherein said medical parameters comprise parameters indicative of vital signs sampled at intervals of less than 10 minutes to be suitable to support critical care decision making in at least one of, (a) an emergency room, (b) an intensive care unit, (c) an operating room and (d) another clinical care delivery setting.

11. A system according to claim 8, including
a workflow processor for identifying task sequences to be performed in critical care treatment in response to a received command and
said decision processor is responsive to a command from said workflow processor in supporting treatment decision making concerning a patient medical condition.

12. A system according to claim 8, including
a workflow processor for generating task sequences to be performed in critical care treatment, said task sequences being generated in response to incorporate identified improvement derived from statistical analysis of treatment and associated outcome data in said treatment information database.

13. A system according to claim 8, including
an update processor for initiating updating of said patient record information to record a determined treatment.

14. A medical information system for processing information from a plurality of sources suitable for use in critical clinical care delivery, comprising:
a communication interface for receiving medical parameters from patient monitoring devices attached to a patient and for bidirectionally communicating with a hospital information database containing patient records;
a data processor using said communication interface for acquiring patient record information from said hospital information database and for collating and storing received patient medical parameters from monitoring devices; and
a data analysis unit for identifying alternative treatment options, by comparing acquired medical parameters received from said monitoring devices with a metric derived by correlating historical data comprising stored parameters and corresponding medical outcomes, said medical parameters being acquired independently of patient interaction and processed by said data analysis unit to support identification of alternative treatment options concurrently with patient monitoring.

15. A system according to claim 14, wherein
said data analysis unit includes a data mining unit for analyzing stored patient parameters by searching for patterns in stored patient parameters and corresponding medical outcomes to identify statistically significant data correlation.

16. A system according to claim 14, wherein
said data analysis unit identifies alternative treatment options using information acquired from a plurality of sources by a data aggregation unit, said data aggregation unit acquiring information from said plurality of sources using standard medical terminology and medical code sets.

17. A system according to claim 16, wherein
said data aggregation unit includes a map associating medical codes of a first code set with corresponding codes of a different second code set for use in associating information elements from different sources.

18. A system according to claim 14, including
a repository of accumulated utilization data determining usage rates of at least one of, (a) medical goods and (b) medical services in treatment of different medical conditions for a plurality of patients and
a data resource analyzer for analyzing said utilization data to identify a cost threshold representative of an expected cost limit and for using said threshold in identifying a treatment case exceeding said expected cost limit.

19. A system according to claim 14, including
a workflow processor for identifying task sequences to be performed in critical care treatment in response to a received command and
said data analysis unit is responsive to a command from said workflow processor in supporting alternative treatment identification.

20. A method for use by a medical information system for processing information from a plurality of sources for use in critical clinical care delivery, comprising the steps of:
receiving medical parameters from patient monitoring devices attached to a particular patient;
bidirectionally communicating with a hospital information database containing patient records;
collating and storing received medical parameters for said particular patient from monitoring devices; and
supporting making of a treatment decision concerning a patient medical condition by suggesting at least one treatment, concurrently with patient monitoring, and based on passively acquired medical parameters received from said monitoring devices independently of patient interaction.

21. A method for use by a medical information system for processing information from a plurality of sources suitable for use in critical clinical care delivery, comprising the steps of:
receiving medical parameters from patient monitoring devices and information from a treatment information database;
bidirectionally communicating with a hospital information database containing patient records to acquire patient record information for a particular patient; and
supporting making of a treatment decision concerning a patient medical condition concurrently with patient monitoring by suggesting at least one treatment based on,
passively acquired medical parameters received from said monitoring devices in substantially real-time and independently of patient interaction and
said acquired particular patient record information and information from said treatment information database.

22. A method for use by a medical information system for processing information from a plurality of sources suitable for use in critical clinical care delivery, comprising the steps of:
receiving medical parameters from patient monitoring devices attached to a patient, bidirectionally communicating with a hospital information database containing patient records;
acquiring patient record information from said hospital information database;
collating and storing received patient medical parameters from monitoring devices;
deriving a metric by correlating historical data comprising stored parameters and corresponding medical outcomes; and
identifying alternative treatment options by comparing acquired medical parameters received from said monitoring devices with said metric, said medical parameters being acquired independently of patient interaction to support identification of alternative treatment options concurrently with patient monitoring.

* * * * *